(12) United States Patent
Sadowski et al.

(10) Patent No.: US 10,646,662 B2
(45) Date of Patent: May 12, 2020

(54) INTRADERMAL INJECTOR

(71) Applicant: Antares Pharma, Inc., Ewing, NJ (US)

(72) Inventors: Peter L. Sadowski, Woodbury, MN (US); Paul R. Lesch, Lino Lakes, MN (US); David L. Bremseth, Plymouth, MN (US)

(73) Assignee: Antares Pharma, Inc., Ewing, NJ (US)

( * ) Notice: Subject to any disclaimer, the term of this patent is extended or adjusted under 35 U.S.C. 154(b) by 0 days.

(21) Appl. No.: 15/681,664

(22) Filed: Aug. 21, 2017

(65) Prior Publication Data

US 2017/0340838 A1 Nov. 30, 2017

Related U.S. Application Data

(63) Continuation of application No. 15/090,812, filed on Apr. 5, 2016, now Pat. No. 9,737,670, which is a continuation of application No. 14/311,332, filed on Jun. 22, 2014, now Pat. No. 9,333,309, which is a continuation of application No. 13/857,438, filed on Apr. 5, 2013, now Pat. No. 8,758,299, which is a continuation of application No. 13/427,969, filed on
(Continued)

(51) Int. Cl.
| | |
|---|---|
| *A61M 5/32* | (2006.01) |
| *A61M 5/20* | (2006.01) |
| *A61M 5/42* | (2006.01) |
| *A61M 5/31* | (2006.01) |
| *A61M 5/24* | (2006.01) |

(52) U.S. Cl.
CPC ........ *A61M 5/3204* (2013.01); *A61M 5/2033* (2013.01); *A61M 5/3134* (2013.01); *A61M 5/425* (2013.01); *A61M 5/2046* (2013.01); *A61M 5/2053* (2013.01); *A61M 5/2459* (2013.01); *A61M 5/3202* (2013.01); *A61M 5/326* (2013.01); *A61M 2005/206* (2013.01); *A61M 2005/2073* (2013.01); *A61M 2005/3118* (2013.01)

(58) Field of Classification Search
CPC .............. A61M 5/3204; A61M 5/2033; A61M 5/3134; A61M 5/425
USPC ........................................................ 604/115
See application file for complete search history.

(56) References Cited

U.S. PATENT DOCUMENTS

| | | | | |
|---|---|---|---|---|
| 3,882,863 A | * | 5/1975 | Sarnoff ............... | A61M 5/2033 604/136 |
| 4,624,660 A | * | 11/1986 | Mijers ................. | A61M 5/2033 604/136 |

(Continued)

*Primary Examiner* — Phillip A Gray

(74) *Attorney, Agent, or Firm* — Morgan, Lewis & Bockius LLP

(57) ABSTRACT

An injection device that comprises a chamber configured for containing a substance to be injected and a needle operatively associated with the chamber and having a length sufficient to deliver the substance to an intradermal injection site. A collar surrounds the needle, defining a collar cavity. The collar also has a peripheral forward skin-contacting surface that surrounds and is radially spaced from the needle and injection site by an area that is sufficiently large to allow a patient's skin to move into the collar cavity to properly position the needle for intradermal delivery of the substance to the injection site to allow spread of the injected substance under the skin while inhibiting or preventing backpressure within the skin from forcing the substance out through the injection site.

10 Claims, 4 Drawing Sheets

Related U.S. Application Data

Mar. 23, 2012, now Pat. No. 8,419,686, which is a continuation of application No. 10/154,412, filed on Aug. 11, 2004, now Pat. No. 8,162,886, which is a continuation of application No. PCT/US03/03917, filed on Feb. 11, 2003.

(60) Provisional application No. 60/355,926, filed on Feb. 11, 2002.

(56) References Cited

U.S. PATENT DOCUMENTS

| | | | | |
|---|---|---|---|---|
| 5,451,210 A | * | 9/1995 | Kramer | A61M 5/1723 604/136 |
| 5,616,128 A | * | 4/1997 | Meyer | A61M 5/2033 604/139 |

* cited by examiner

INTRADERMAL INJECTOR

CROSS REFERENCE TO RELATED APPLICATIONS

This application is a continuation of U.S. patent application Ser. No. 15/090,812, filed Apr. 5, 2016, which is a continuation of U.S. patent application Ser. No. 14/311,332, filed Jun. 22, 2014, which issued as U.S. Pat. No. 9,333,309 on May 10, 2016, which is a continuation of U.S. patent application Ser. No. 13/857,438, filed Apr. 5, 2013, which issued as U.S. Pat. No. 8,758,299 on Jun. 24, 2014, which is a continuation of U.S. patent application Ser. No. 13/427,969, filed Mar. 23, 2012, which issued as U.S. Pat. No. 8,419,686 on Apr. 16, 2013, which is a continuation of U.S. patent application Ser. No. 10/915,412, filed Aug. 11, 2004, which issued as U.S. Pat. No. 8,162,886 on Apr. 24, 2012, which is a continuation of International Patent Application No. PCT/US03/03917 filed Feb. 11, 2003, which claims priority of U.S. Provisional Application No. 60/355,926 filed Feb. 11, 2002, the contents of which applications are expressly incorporated herein by reference thereto.

FIELD OF THE INVENTION

The present invention relates to a injection device. More particularly, the invention relates to an intradermal injector to minimize bubbling or blistering of the skin during injection.

BACKGROUND OF THE PRESENT INVENTION

It has been found that intradermal delivery of certain substances and vaccines is more effective than when it is delivered intramuscularly. While traditional jet injectors are known for injecting a substance intradermally, they are not capable of properly providing an intradermal injection.

Jet injectors utilize the stream of the injected substance to overcome the resistance of the skin to penetration. This high velocity stream of substance then also constitutes the substance to be delivered. Traditional jet injectors require high energy to penetrate the top layers of the skin which provide most of the resistance. Providing sufficient power for such penetration and then depositing the material to be injected just under the surface skin layer, such as what is required for an intradermal injection is challenging. An injection weak enough to administer the material intradermally may be so weak that not all the substance is delivered as the skin surface is not completely penetrated by the jet. An injection may be to sufficient to deliver the entire substance but so strong that most of the injected substance is delivered much deeper than the superficial layers of the skin.

Traditional needle injection methods aimed at delivering a substance intradermally also suffer from major shortcomings. They require a lot of skill on the part of the person delivering the injection as careful placement of the needle as part of the insertion process is required. Injecting the substance to fast from a traditional device by pushing on substance being pushed back out of the injection hole once the needle is removed. The patient is not comfortable during what seems like a long injection due to the desire to deliver the injected substance slowly to prevent the substance from coming back out of the injection site. Thus improvements in intradermal injectors are needed.

SUMMARY OF THE INVENTION

The invention relates to an injector, which is preferably an intradermal injection device. A preferred embodiment of the injector includes a chamber configured for containing a substance to be injected. A needle is operatively associated with the chamber and has a length sufficient to deliver the substance to an intradermal injection site. A collar surrounds the needle and defines collar cavity. The collar has a peripheral forward skin-contacting surface that surrounds and is radially spaced from the needle and injection site by an area that is sufficiently large to allow a patient's skin to move into the collar cavity to properly position the needle for intradermal delivery of the substance to the injection site and to allow spread of the injected substance at the injection site so as to inhibit or prevent backpressure causing the injected substance to flow out of the hole created in the skin by the needle after the injection. An energy source preferably is associated with the needle to assist in delivering the substance to the injection site. The preferred energy source is configured to provide an injection assisting pressure of between about 50 and 300 psi to the substance.

In this embodiment, the collar has a circular peripheral surface and an internal diameter of about 4 mm to 7 mm, and the skin-contacting surface of the collar is discontinuous. The skin-contacting surface can define discontinuity gaps, with the skin-contacting surface and gaps together defining a closed shape. The skin-contacting surface preferably occupies at least about 50% of the closed shape. Additionally, the closed shape is preferably rounded, but may alternatively be given other suitable shapes. A preferred shape is circular, and the discontinuity gaps preferably are substantially equally spaced along the shape, more preferably with at least two substantially equally sized continuous portions separated by the discontinuity gaps. The preferred needle is configured so that the distal, delivery end thereof is disposed within about 0.5 mm of the forward end of the skin-contacting surface.

The invention also relates to a method of intradermal administration of a substance. In the preferred method, a substance is delivered to an intradermal injection site through a needle while contacting the skin with a surface that is spaced from the needle by an area surrounding the needle and injection site. The area is sufficiently large to allow the substance to be intradermally injected without causing back pressure at the injection site in the patient's skin to force any substantial amount of the injected substance out of the needle hole. The delivery of the substance is preferably assisted by applying a pressure to the substance, preferably about between 50 and 300 psi. The needle can be moved from a retracted position to an extended position in which the needle is exposed for injecting the substance into the patient by drivingly associating a pressurized gas source therewith, the gas can be vented when the substance is injected, and the needle can be biased with a resiliently deformed resilient member to retract the needle when the gas is vented.

The needle of one injector embodiment has a retracted position, which can be within the injector body, and also has an extended position, in which the needle is disposed for penetrating a patient and injecting the substance. A resilient needle cap covers the sharp needle end and is disposed and configured such that the cover is resiliently deformed with the needle in the extended position for biasing the needle from the extended position towards the retracted position. Preferably, the needle is disposed for piercing the cap when moved from the retracted position to the extended position. Additionally, one embodiment has a gas chamber containing a compressed gas and a plunger biased by the compressed gas with respect to the substance to be delivered, for forcing the substance through a delivery conduit, such as a needle, for the injecting of the substance. The plunger and the gas chamber are associated such that once the plunger is moved to a predetermined position to inject a predetermined amount of the substance, the compressed gas is released from the gas chamber to allow the cap or other resilient member used to retract the needle.

DETAILED DESCRIPTION OF THE PREFERRED EMBODIMENTS

Figure 1:
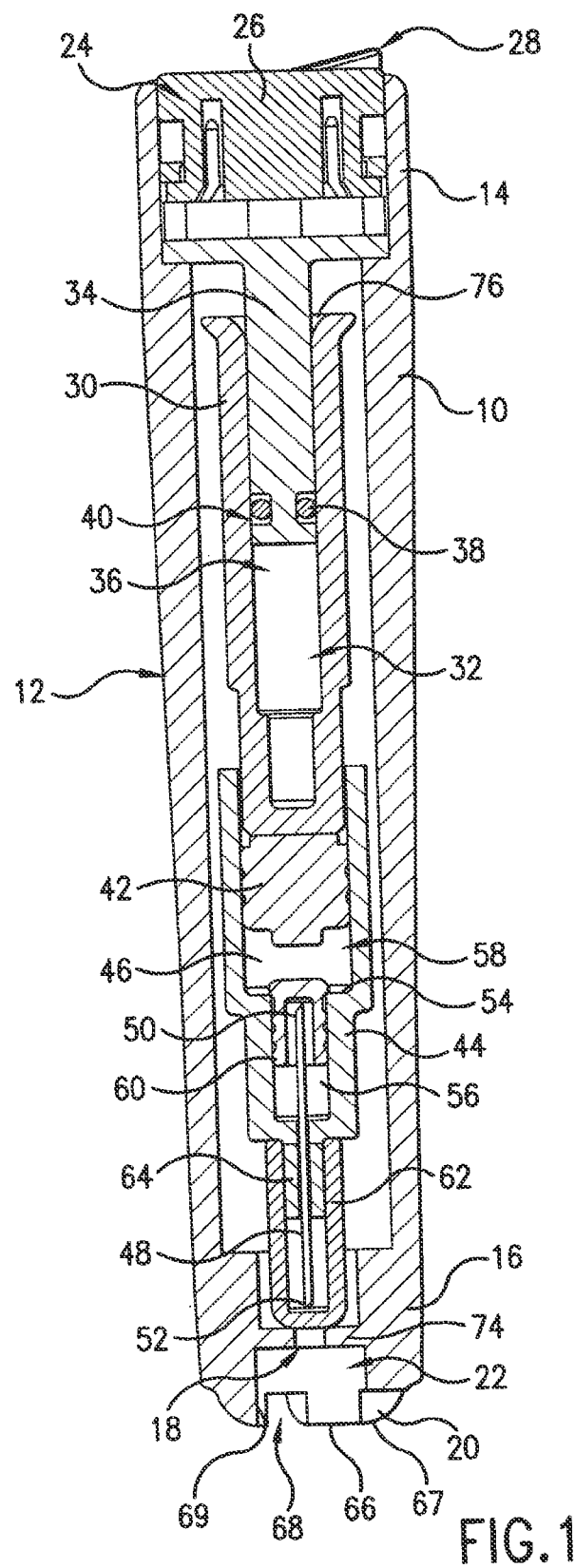
FIG. 1 is a cross-sectional view of a preferred embodiment of an injector constructed according to the present invention.
Figure 2:
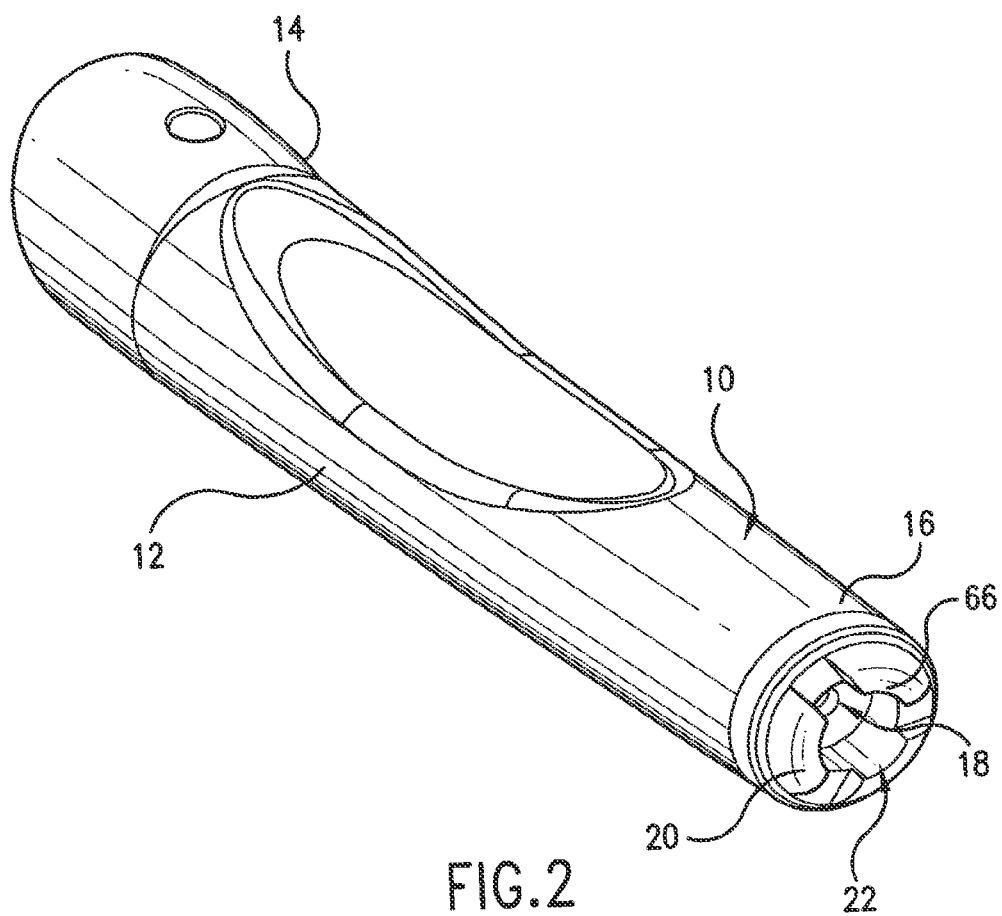
FIG. 2 is a perspective view thereof.
Figure 3:
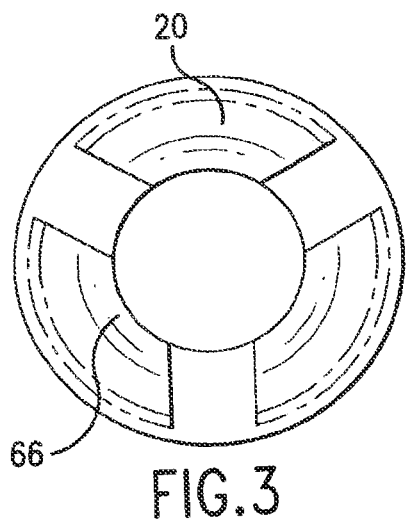
FIGS. 3 and 4 are distal end and perspective views, respectively, of the distal end thereof.
Figure 4:
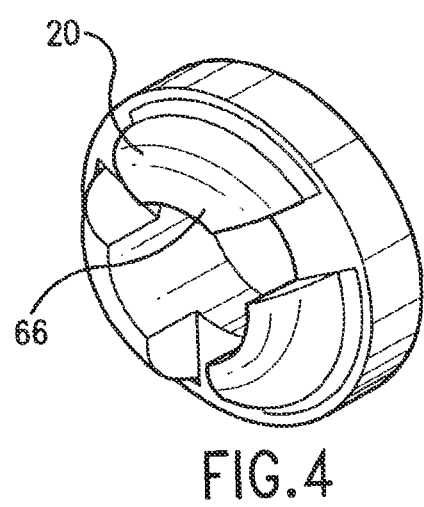

In the embodiment shown in FIG. 1, the outer housing 10 includes a preferably elongated and cylindrical body 12 with proximal and distal ends 14,16. As used with respect to the embodiments in this application, the term "distal" designates the end or direction toward the front of injector, and the term "proximal" designates the end or direction toward the rear of the injector. A needle opening 18 is disposed at the forward or distal end of the housing 10 and is configured and dimensioned for receiving an injection needle that extends from the interior of the housing.

A trigger assembly 24 is preferably disposed at the proximal end 14, although in other embodiments is disposed in other portions of the injector, including at the distal end. The trigger assembly 24 includes a button 26, which is depressible into the housing 10, preferably axially, to fire the injector. The trigger assembly 24 preferably includes a safety lock to selectively prevent the injector from firing. In the embodiment shown, safety lock 28 is constructed as part of the button 26, and can be rotated axially between locked and unlocked positions to prevent or allow firing of the injector, respectively.

The button 26 is associated with a firing latch that retains a firing member in a loaded position. The firing member preferably comprises a firing cylinder 30, which is shown in the loaded position in FIG. 1. The preferred firing cylinder 30 is substantially cylindrical, with large and small diameter sections both in the interior bore 32 and also on exterior thereof, although other embodiments have a single inner and outer diameter or other shapes.

Firing cylinder bore 32 receives piston 34, which is preferably fixed to the outer housing 10. The piston 34 is received in the cylinder bore 32 preferably in leak tight association to retain a sufficient amount and pressure of compressed gas in a gas chamber 36, defined between the bore 32 and piston 34, to fire the injector. The compressed gas can be provided in a compressed state or can be a product of a reaction of a gas generator therein, such as one activated upon firing of the injector. A seal 38, such as an o-ring, is preferably disposed in a groove 40 on the piston to seal the gas in the gas chamber 36. A preferred gas in carbon dioxide, although other suitable gases can be used. Alternative embodiments employ different energy sources to fire the injector, such as coil springs.

A plunger 42 is disposed ahead of the firing cylinder 30 and operatively associated therewith so that the firing cylinder 30 forces the plunger 42 in a distal direction when the injector is fired. The plunger 42 is received within a medicament cartridge 44, which preferably contains a medicament, but alternatively contains another suitable fluid. As shown in FIG. 1, the plunger 42 is disposed in a large diameter portion 46 of the medicament cartridge 44.

A hollow injection needle 48 is open to the interior of the medicament cartridge 44, and is preferably fixed thereto with a proximal sharp end 50 protruding into the interior of the cartridge, and a distal sharp end 52 protruding beyond the medicament cartridge 44 in alignment with the needle opening 18. In the preferred embodiment, the proximal sharp end 50 of the needle 48 is disposed distally from shoulder 54, which separates the large diameter portion 46 from a narrow diameter portion 56 and is configured to stop the motion of the plunger 42 in the distal direction upon contact therewith.

A stopper 60 is disposed in the medicament cartridge 44, preferably in the narrow portion 56. The stopper 60 seals a medicament chamber 58, which, in the loaded position shown, is defined between the plunger 42 and the stopper 60 within the medicament cartridge 44, in the large diameter portion 58. Also, in the loaded position, the stopper 60 separates the medicament chamber 58 from the needle 48.

A needle cap 62 is disposed around the needle 48, preferably between the needle 48 and the needle opening 18, surrounding the front of the distal sharp end 52. The embodiment shown has the needle cap 62 fitted to a needle holder extension 64 of the medicament cartridge 44. The needle cap 62 is preferably sufficiently resilient to bias and retract the cartridge 44 and needle 48 in a proximal direction, towards the proximal end 14. An alternative embodiment has a needle cap that is mounted outside of the outer housing. This alternative embodiment preferably has a resilient element to bias the cartridge and needle in a proximal direction.

Referring to FIGS. 1-4, a collar 20 preferably surrounds the needle opening 18 on the outside of the outer housing 10. A collar cavity 22 is defined within the collar 20, and is preferably substantially coaxial therewith and with the needle opening 18. The collar 20 has a peripheral skin-contacting surface 66 that surrounds and is radially spaced from the needle 48 and needle opening 18. This spacing, as well as the axial depth of the collar cavity are selected to space the skin-contacting surface 66 from the injection site by an area that is sufficiently large to allow a patient's skin to move into the collar cavity 22 to properly position the needle for intradermal delivery of the substance to the injection site, preferably without causing a blister or bubble in or under the patient's skin, and to allow spread of the injected substance under the skin while inhibiting or preventing backpressure within the skin from forcing the substance out through the injection site.

The configuration of the injector collar 20 affects the intradermal placement of the injected substance or medicament. If the collar 20 and collar cavity 22 is too small in diameter, the substance can be injected in the form of a blister or bubble that will stretch the outer layer of skin like a balloon. When the injector is removed, the substance can immediately exit the bubble through the needle hole, thus losing some or all of the substance from the injection. The preferred skin-contacting surface 66 is configured to reduce or eliminate this blistering or bubbling effect.

The preferred collar 20 and skin-contacting surface 66 have a closed shape and are rounded, such as having a circular or generally oval perimeter that contacts the patient's skin. In the embodiment of FIGS. 1-4, this perimeter is circular. For most vaccine injections made on the arms or legs of a person, a diameter of at least about 4 mm is desired. Diameters about between 2 mm and 10 mm are preferred, and generally, diameters of about between 4 mm and 7 mm are most useful, depending upon the substance to be injected.

In the preferred embodiment, the collar 20 and skin-contacting surface 66 are discontinuous and define discontinuity gaps 68 that divide the skin-contacting surface 66. The skin-contacting surface 66 is disposed surrounding the needle opening 18, preferably occupying angularly at least about 50%, and more preferably at least about 65% and at most about 90%, of a phantom closed, continuous shape surrounding needle opening 18 that is defined by the combination of the skin-contacting surface 16 and the gaps 68. The preferred collar 20 defines two, three, or more gaps 68, or cutout portions of the collar 20, while leaving sufficient surface area of the skin-contacting surface 66 to properly position the injector on the skin of the patient without causing discomfort and while providing sufficient contact to stretch the skin to enable correct placement of the injection. When the collar 20 or skin-contacting surface 66 is circular, it is preferred to provide substantially equal amounts of removed areas or gaps 68 in positions that are equally spaced around the periphery of the collar 20. An alternative embodiment has a substantially continuous collar with no gaps. The preferred collar 20 has an outer wall 67 with a rounded cross-section, and a substantially flat and axial inner wall 69, and which is preferably disposed at an angle of less than about 20° from the axis. In other embodiments, all walls can be rounded, all flat, or the inner wall can be rounded and the outer wall flat, depending on the intended use.

Figure 5:
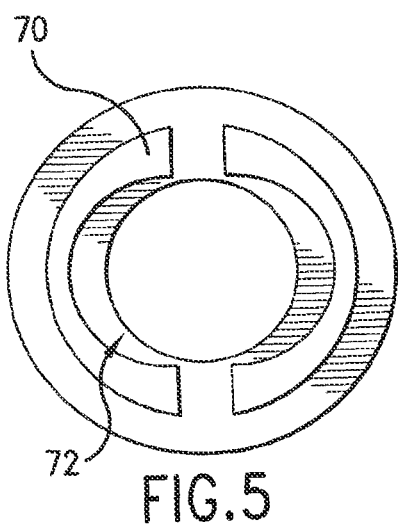
FIGS. 5 and 6 are distal end and perspective views, respectively, of an alternative embodiment of a distal end of an injector.
Figure 6:
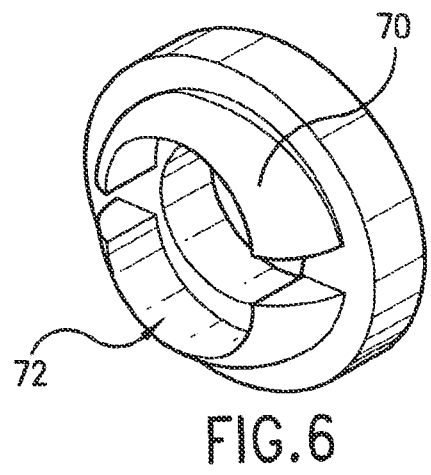

In another embodiment, a smaller diameter circular or oval collar can be utilized, with a discontinuous skin-contacting surface. This can be achieved by arranging spaced portions of the surface, or by removing portions of the surface. This lessens the force of the collar on the skin to allow the injection to be properly placed between the dermal layers. One desirable arrangement is an evenly divided circular collar that has two equal sized halves of about 7 mm outer diameter with an internal opening of about 4 mm. Another embodiment has an oval collar divided along its major or minor axis, or along both. The embodiment of FIGS. 5 and 6 has a collar 70 that defines an oval collar cavity 72 divided along its minor axis, although the outside of the collar has a substantially circular shape. Thus, the thickness of collar 70 varies along its periphery.

The skin-contacting surface is configured to contact the skin, as its name implies. The gaps are configured to release pressure at specific locations on the skin, and preferably to remain of contact with the skin when the injector is pressed against the skin for the injection. In the embodiment shown, the skin-contacting surface 66 is substantially planar, although other suitable shapes can be used.

Figure 7:
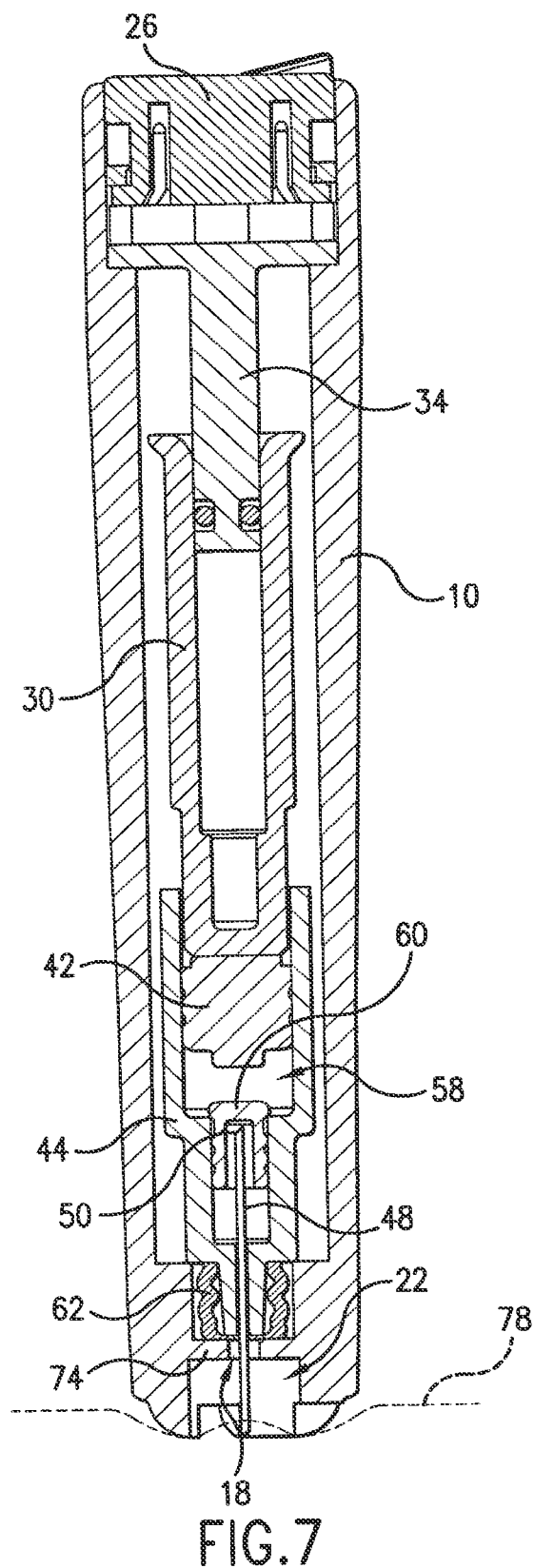
FIG. 7 is a cross-sectional view of the injector of FIG. 1 during the firing thereof.

With reference to FIGS. 1 and 7, to use the injector, the collar 20 is placed against a user's skin 78, which enters the collar cavity 22. The button 26 is depressed, which causes the latch to release the firing cylinder 30. The compressed gas in the gas chamber 36 acts against the piston 34 and firing cylinder 30 to bias and move the firing cylinder 30 distally, as shown in FIG. 7. The firing cylinder 30 in turn forces the plunger 42 distally, which biases the fluid in the medicament chamber 58 and the medicament cartridge 44, which compresses the needle cap 62 against distal wall 74 of the outer housing 10. The needle 48 is thus moved from the retracted position shown to an extended position through the needle opening 18, into the collar cavity 72, and a predetermined distance into the user's skin 78. As piston 42 travels in the distal direction, it moves the fluid in the medicament chamber 58 distally, causing the stopper 60 to move distally as well. The stopper 60 is then pierced by the proximal end 50 of the needle 48, placing the interior of the needle 48 and the medicament chamber 58 in fluid communication. Continued distal movement of the plunger 60 injects the fluid through the needle 48 into the user's skin.

The firing cylinder 30 and the piston 34 are preferably configured to release the compresses gas from the gas chamber 36. In the embodiment shown, the length of the firing cylinder 30 and the piston are selected so that beveled portion 76 at the proximal side of the firing cylinder 30 is disposed past the seal at the distal side of the piston 34, releasing the seal and letting the compressed gas escape. When the gas escapes, reducing the pressure within the gas chamber 36, the resilient needle cap 62, or an alternative spring used, retracts the medicament cartridge 44 and needle 48 in a proximal direction, back into the housing 10. This arrangement can also be used for firing and releasing gas pressure from an energy source in a jet injector.

In the extended position, the needle 48 can be disposed towards the proximal or distal sides of the forward end of the skin-contacting surface 66 or substantially flush therewith, depending on the intended use. In one preferred embodiment, the needle 48 is disposed at most about 1 mm behind or proximally from the forward end of the skin-contacting surface 66 and more preferably at most about 0.5 mm, and at least about flush therewith and more preferably at least about 0.2 mm proximally therefrom. In another preferred embodiment, the needle 48 is disposed at most about 1 mm ahead of or distally from the forward end of the skin-contacting surface 66 and more preferably at most about 0.5 mm, and at least about flush therewith and more preferably at least about 0.2 mm or 0.3 mm distally therefrom. One flush embodiment has the needle 48 in the extended position disposed between about 0.2 mm to either side of the forward end of the skin-contacting surface 66, more preferably within 0.1 mm, and most preferably within about 0.05 mm or better. In one embodiment, the position of the distal end of the 48 with respect to the skin-contacting surface 66 and the shape and size of the collar 20 and skin-contacting surface 66 are selected so that the injection depth into the patient at the injection site is around 0.2 inches.

The fluid substance to be delivered is preferably a solution, and more preferably a vaccine in liquid form. As noted above, it has been found that the intradermal delivery of a vaccine is more effective than when it is delivered intramuscularly. Relatively small amounts are administered, typically on the order of about 50 microliters, although the device can be designed to administer between about 25 and 100 microliters.

In the preferred embodiment of the present invention, a jet spray is not necessary, but may be used in an alternative embodiment. The preferred intradermal injection of the substance is assisted by a low pressure. While this pressure varies depending upon the length of the needle protruding from the injection device, a range of pressures between about 50 and 300 psi is generally sufficient to properly administer the substance to the desired position and location. In embodiments intended to inject the fluid no further than the dermis, high pressures that inject the substance below the dermis rather than between dermal layers, such as those obtainable by conventional needle free injection devices, should be avoided or else the substance will be placed too deeply, thus defeating the purpose for the intradermal injection. Preferably, the pressure assisted injection is made at pressures of between 65 and 250 psi, more preferably between 75 and 150 psi.

This pressure is easily achieved in a device that includes an energy source, such as a coil spring, gas propellant, or a gas spring such as described above. The collar may even be provided on a syringe with the pressure being provided by the strength of the user's thumb in depressing a plunger by a predetermined distance which corresponds to the delivery of the desired amount of substance. The collar assures that the needle is positioned appropriately so that the substance is delivered properly to the desired location.

In one embodiment, the injection device includes a housing with a skin contacting collar at a distal end of the injector; a retractable injection-assisting needle at a distal end of the injector; a fluid chamber having an opening for slidingly receiving at least a portion of the needle; a plunger movable in the fluid chamber; a trigger assembly; and a energy source operatively associated with the trigger assembly so that movement of the trigger assembly activates the energy source to move the plunger in a first direction to expel a fluid from the fluid chamber. The retractable injection-assisting needle has a needle tip located at a distal end of the needle and a discharge channel within the needle tip terminating in an orifice through which the fluid is expelled. The needle is located within the housing in a retracted position prior to activation of the energy source. Movement of the plunger in the first direction upon activation of the energy source results in at least a portion of the needle moving forward into the skin contacting collar to a needle insertion point, and expelling fluid through the needle tip and past the needle insertion point to a needle injection site. The needle insertion point is located at the needle tip, and the needle injection site is distal to the needle tip. The retraction element returns the needle tip to the retracted position inside the housing after activation of the energy source.

Other suitable injection devices that can be modified to include a collar with a skin-contacting surface are described in U.S. application Ser. No. 09/779,603, filed on Feb. 9, 2001, the content of which is hereby incorporated herein by reference thereto.

While illustrative embodiments of the invention are disclosed herein, it will be appreciated that numerous modifications and other embodiments may be devised by those skilled in the art. For example, the discontinuity gaps in the collar may be other than sheer cutouts from the collar. The collar may have protruding portions and adjacent recessed portions, which are the gaps and which may have a continuous surface with the protrusions around the perimeter and shape followed by the collar. Therefore, it will be understood that the appended claims are intended to cover all such modifications and embodiments that come within the spirit and scope of the present invention.

What is claimed is:

1. An injection device, comprising:
   a housing;
   a chamber within the housing, the chamber configured for containing a substance to be injected;
   a needle having a delivery end, the needle being operatively associated with the chamber and configured to deliver the substance to an intradermal injection site, the needle configured to move between a retracted position and an extended position in which the needle is disposed for penetrating a patient and injecting the substance;
   a resilient needle cap covering the delivery end in the retracted position, wherein the resilient needle cap is in a relaxed configuration when the needle is in the retracted position and a compressed configuration with the needle in the extended position, wherein the resilient needle cap moves from the compressed configuration toward the relaxed configuration after an injection thereby retracting the needle from the extended position towards the retracted position; and
   a collar surrounding the needle and defining a collar cavity, the collar having a peripheral forward skin-contacting surface that surrounds and is radially spaced from the needle and injection site by an area that is sufficiently large to allow a patient's skin to move into the collar cavity,
   wherein the delivery end of the needle is within the collar cavity when the substance is delivered to the intradermal injection site.

2. The injection device of claim 1, wherein the needle is disposed for piercing the resilient needle cap when the needle moved from the retracted position to the extended position.

3. The injection device of claim 2, further comprising:
   a gas chamber containing a compressed gas; and
   a plunger biased by the compressed gas with respect to the substance for forcing the substance through the delivery end for injecting of the substance, wherein the plunger and the gas chamber are associated such that once the plunger is moved to a predetermined position to inject a predetermined amount of the substance, the compressed gas is released from the gas chamber to allow the resilient needle cap to retract the needle.

4. The injection device of claim 1, wherein the collar cavity is configured to allow delivery of the substance to the injection site to allow spread of the substance under the skin while inhibiting or preventing backpressure within the skin from forcing the substance out through the injection site.

5. The injection device of claim 1, wherein the needle pierces the resilient needle cap as the needle moves from the retracted position to the extended position.

6. The injection device of claim 1, further comprising a circumferentially discontinuous collar surrounding the needle and defining a collar cavity,
   wherein the circumferentially discontinuous collar is disposed on an exterior surface of the housing and radially spaced from and at least partially surrounding the needle such that a patient's skin can move into the collar cavity to properly position the needle for intradermal delivery of the substance to the injection site.

7. The injection device of claim 1, further comprising a stopper sealing the chamber, the stopper separating the needle from the chamber in the retracted position, wherein the stopper is configured to be pierced by the needle with the needle in the extended position to place the chamber in fluid communication with the needle.

8. The injection device of claim 7, wherein the chamber includes a first portion having a first diameter and a second portion having a second diameter, wherein the first diameter is larger than the second diameter.

9. The injection device of claim 8, wherein the stopper seals the second portion and a plunger seals first portion.

10. The injection device of claim 9, wherein a proximal end of the needle is within the second portion when the needle is in the retracted position.

* * * * *